United States Patent [19]

Grollier et al.

[11] 4,357,141

[45] Nov. 2, 1982

[54] COMPOSITIONS FOR DYEING HAIR AND THEIR APPLICATIONS

[75] Inventors: Jean-Francois Grollier, Paris; Christian Monnais, Neuilly-sur-Seine; Lyonel Peritz, Boulogne-sur-Seine, all of France

[73] Assignee: L'Oreal, Paris, France

[21] Appl. No.: 147,330

[22] Filed: May 6, 1980

Related U.S. Application Data

[63] Continuation of Ser. No. 940,040, Sep. 6, 1978, abandoned.

[30] Foreign Application Priority Data

Sep. 7, 1977 [FR] France .................................. 77 27096
Jun. 15, 1978 [FR] France .................................. 78 17900

[51] Int. Cl.$^3$ ............................................... D06P 3/04
[52] U.S. Cl. ............................................ 8/406; 8/407; 424/DIG. 2
[58] Field of Search ...................... 8/406; 424/DIG. 2

[56] References Cited

U.S. PATENT DOCUMENTS

| | | | |
|---|---|---|---|
| 2,271,378 | 1/1942 | Searle | 424/78 |
| 3,270,022 | 8/1966 | Wakeman et al. | 424/70 |
| 3,322,676 | 5/1967 | Hiestand | 424/70 |
| 3,530,215 | 9/1970 | Greif et al. | 424/70 |
| 3,986,825 | 10/1976 | Sokol | 8/10.1 |
| 4,009,255 | 2/1977 | Kalopissis et al. | 8/10.1 |

FOREIGN PATENT DOCUMENTS

2270846 12/1975 France .
2316271 1/1977 France .

*Primary Examiner*—Dale R. Ore
*Attorney, Agent, or Firm*—Cushman, Darby & Cushman

[57] ABSTRACT

Creams and gelatinizable liquid which contain oxidation dyes and a vehicle, useful for dyeing hair, are disclosed. The vehicle includes at least one fatty acid, at least one alkalizing agent and at least one cationic polymer containing repeating units of the formula:

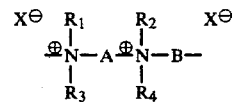

21 Claims, No Drawings

COMPOSITIONS FOR DYEING HAIR AND THEIR APPLICATIONS

This is a continuation of application Ser. No. 940,040 filed Sept. 6, 1978, now abandoned.

The present invention is directed to compounds for dyeing hair, to compositions containing said compounds and to the use of said compounds for dyeing hair.

According to current practices, oxidation hair dyes are used for dyeings which are resistant, for several weeks, to shampoo, light and weather conditions.

Said oxidation dyes are based on aromatic compounds of the diamine, aminophenol or phenol type. Said compounds are not generally dyes per se but are converted into dyes, by condensation in the presence of an oxidizing medium, generally formed of oxygenated water. Oxidation dyes can be classified as "bases" which are para- or ortho-derivatives of the diamines and aminophenols and as "couplers" (or modifiers) which are meta derivatives including, for instance, meta-diamines, m-aminophenols or polyphenols.

The color of the oxidation dyes is developed in the presence of hydrogen peroxide in a basic medium, generally ammoniacal, which allows both decoloring the hair and dyeing it to the desired color. The oxidation dye dyeing operation is in fact a complex operation which encompasses both a decoloration (lightening or stripping) action and the dyeing action itself.

The dye compositions, also referred to as dye vehicles or dye carriers, may take the form of creams or of liquids gelatinizable by dilution.

Generally, said creams contain either fatty acid soaps containing 12 to 18 carbon atoms or fatty alcohols in the presence of anionic or nonionic emulsifiers.

Generally, the gelatinizable liquid contains either nonionic oxyethylenated or polyglycerolated compounds and solvent or liquid fatty acid soaps, such as oleic acid or isostearic acid, and solvent.

Alkalizing agents used to make soaps include potash, soda, ammonia, monoethanolamine, diethanolamine or triethanolamine.

By employing oxygenated water at the dilution ratios most frequently employed (from 1 to 3 times) so as to obtain a composition containing sufficient quantities of oxygenated water and ammonia to obtain lightening, the dye vehicles in the form of a cream yield a cream while the dye vehicles in the form of a gelatinizable liquid yield a gel.

These vehicles can be improved by the addition of cations which favor the disentangling of wet hair and provide dry hair with a certain softness and a certain shine.

Often, dye compositions in the form of creams are used to provide white hair with good coverage but with attendant detriment to the luminosity of sheen, while gelatinizable liquid dye compositions result in very luminous nuances but provide inferior coverage of white hair, compared to the creams.

The invention resides in the discovery that especially interesting results are obtained by preparing a composition for oxidation dyeing, which is to be diluted with an oxidizing solution, by admixing at least one fatty acid, at least one cationic polymer of a special class, benzyl alcohol and at least one alkalizing agent optionally in a mixture containing the conventional ingredients of a dye vehicle, including the dye(s), thickener(s), solvent(s), sequestering agent(s), anti-oxidizing agent(s) and the like.

The hair dyeing composition of the invention is characterized by effecting less damage to hair compared to products currently in use.

The hair dyeing composition of the invention also confers excellent disentangling properties and a pleasant feel to wet or dry hair.

After hair is dyed with the composition of the invention, it is strong, fluffy, shiny and non-electric.

Furthermore, the coloring resulting from use of the dye vehicle is especially remarkable in providing good coverage as well as luminosity and sheen, to white hair and provides nuances uniformly, while being resistant to light and shampoo.

The invention is particularly directed to a hair dye composition which is to be diluted with an oxidizing solution, containing at least one oxidation dye and a vehicle wherein the vehicle comprises at least one fatty acid, at least one alkalizing agent in an amount which is in excess of the stoichiometric quantity necessary for neutralizing the fatty acid, benzyl alcohol in an amount of from 2 to 20% by weight of the composition and at least one cationic polymer, present in an amount of from 1 to 15% by weight of the composition, formed of repeating units of the formula

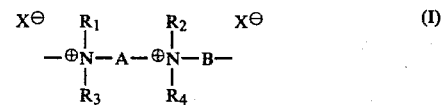

(I)

in which:

$R_1$ and $R_2$ are alkyl of 1 to 3 carbon atoms, and $R_3$ and $R_4$ are alkyl or hydroxyalkyl of 1 to 3 carbon atoms; $R_2$ and $R_4$ may also represent alkyl of 4 to 8 carbon atoms when $R_1=R_3=CH_3$, and in this case $R_2$ and $R_4$ are identical; and $R_4$ may also represent benzyl, cyclohexyl or alkyl of 4 to 12 carbon atoms when $R_1=R_2=R_3=CH_3$;

A and B are the same or different and each of A and B is alkylene or alkenylene, linear or branched, of 2 to 20 carbon atoms; $-(CH_2)_n-O-(CH_2)_n-$, $-(CH_2)_m-NH-CO-NH(CH_2)_m-$, $-CH_2-CH(OH)CH_2-$ or $-CH_2-C_6H_4-CH_2-$; each of n and m is a whole number equal to 2 or 3 and $X^\ominus$ is a cosmetically acceptable anion.

The fatty acid component of the composition contains 12 to 20 carbon atoms, preferably 12 to 18 carbons and can be natural or synthetic fatty acid(s). Examples include lauric acid, myristic acid, palmitic acid, stearic acid, isostearic acid, oleic acid, arachic acid, ricinoleic acid, phenylstearic acid, linoleic acid or mixtures thereof.

The alkalizing agent can be sodium hydroxide, potassium hydroxide, ammonia, monoethanolamine, diethanolamine, triethanolamine or mixtures thereof.

The presence, in the dye vehicle, of at least one fatty acid and at least one alkalizing agent allows formation of a fatty acid soap in situ.

In the dye vehicle of the invention, the concentration in fatty acid (before dilution) is from 5 to 30% and preferably from 10 to 25% by weight.

The alkalizing agent is present in excess of the stoichiometric quantity corresponding to the neutralization of the fatty acid. This excess represents from 1 to 30% of the total weight of the composition (prior to dilution).

Among the polymers having repeating units of Formula I (hereinafter referred to as polymers of Formula I), are those for which (1) $R_1$, $R_2$, $R_3$ and $R_4$ are identical and each is alkyl of 1 to 3 carbon atoms, and (2) $R_1$ is identical to $R_2$ and $R_3$ is identical to $R_4$, with $R_1$ and $R_2$ representing alkyl of 1 to 3 carbon atoms and $R_3$ and $R_4$ representing hydroxyalkyl of 1 to 3 carbon atoms; and more particularly those in which each of $R_1$, $R_2$, $R_3$ and $R_4$ is methyl, ethyl, or propyl or $R_3$ and $R_4$ represent 2-hydroxyethyl, 2-hydroxypropyl or 3-hydroxy propyl, or $R_2$ and/or $R_4$ represent butyl; those in which A and B, identical or different, represent an alkylene of the formula

$$-(CH_2)_y-C(H)(E)-(CH_2)_x-CH(K)-(CH_2)_t-$$

wherein y, x and t are whole numbers which can vary from 0 to 11 and wherein the sum $(x+y+t)$ is greater than or equal to 0 and less than 18, wherein each of E and K is hydrogen or aliphatic, e.g. alkyl, containing less than 18 carbon atoms; those in which A and B, identical or different, represent alkenylene of the formula

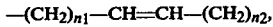

$$-(CH_2)_{n_1}-CH=CH-(CH_2)_{n_2},$$

$n_1$ and $n_2$ being whole numbers can vary from 0 to 18, the sum of which is less than or equal to 18; and those in which $X^\ominus$ is a halide anion, more preferably chloride, bromide or iodide.

The invention does not require use of polymers of a fixed molecular weight.

The quaternized polymers which can be used in the dye compositions of the invention are known or can be prepared by procedures analogous to those described in French Pat. No. 75.15162 (which corresponds to U.S. Application Ser. No. 577,836, filed May 15, 1975) which is incorporated by reference herein, and in French Pat. No. 76.20261, corresponding to U.S. Application Ser. No. 702,924, filed July 6, 1976, also incorporated by reference herein.

Basically the process for forming polymers which are used in the invention includes reacting by polycondensation a di-tertiary diamine of the formula II

$$\begin{array}{cc} R_1 & R_2 \\ | & | \\ N-A-N \\ | & | \\ R_3 & R_4 \end{array} \quad \text{II}$$

with a dihalide of the formula X-B-X, wherein the definitions of A and B are as defined above; the R radicals, which may be different in one compound of formula II, are e.g. aliphatic radicals, cyclohexyl or benzyl; and X is an anion of a mineral acid. The polycondensation reaction is undertaken at a temperature of 10° to 150° C. in a solvent or mixture of solvents such as water, dimethylformamide, acetonitrile, and lower alkanols, e.g. methanol and the like. The two reactants are used in substantially equimolar ratios.

The diamine reactant of the polycondensation can be formed by various methods including (a) by reacting, at 50°–150° C., $R-NH_2$ with a dihalide of the formula Hal-A-Hal, Hal being a halogen ion preferably bromine or iodine and R (taken for $R_1-R_4$ as defined above) and A being as defined above to form an intermediate and then by methylating the intermediate with an excess (2 to 20 moles) of formaldehyde in the presence of formic acid; (b) by reacting a primary amine with an arylsulfonamide to obtain the sulfonamide derivative of the primary amine and by methylating said derivative by treating it with a derivative of an alkali metal and then with, for instance, methyl sulfate; or (c) by reacting a primary amine with an arylsulfonyl halide to produce a sulfonamide derivative of the primary amine; by treating this sulfonamide derivative with Hal-A-Hal, at 80° to 140° C., to form an intermediate and by subjecting said intermediate to acid hydrolysis.

The concentration of polymers (before dilution with the oxidizing agent) used in the composition of the invention is from 1 to 15%, and preferably from 1.5 to 10% by weight of the composition.

Oxidation dyes which may be used in the instant invention include those dyes referred to as "bases", the para- or ortho-derivatives, which are diamines or aminophenols, and those referred to as "couplers", the meta-derivatives, which include diamines, aminophenols and diphenols.

Paraphenylenediamines which may be used in compositions of the invention include primary, secondary or tertiary paraphenylenediamines, optionally substituted on the benzene ring, and preferably those of the formula

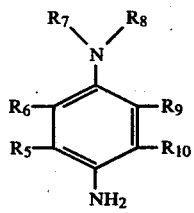

in which $R_7$ and $R_8$, identical or different, represent hydrogen, alkyl of straight or branched chain, mono- or polyhydroxylated alkyl, piperidinoalkyl, carbamylalkyl, dialkyl carbamylalkyl, aminoalkyl, monoalkylaminoalkyl, dialkylaminoalkyl, ω-aminosulfonylalkyl, carboxyalkyl, alkylsulfonamidoalkyl, arylsulfonamidoalkyl, morpholinoalkyl, acylaminoalkyl, sulfoalkyl, or alkoxyalkyl, in which the alkyl includes preferably 1 to 4 carbon atoms, or $R_7$ and $R_8$ together form a heterocyclic group with five or six atoms, such as morpholine or piperidine, each of $R_5$, $R_6$, $R_9$, and $R_{10}$ represents hydrogen or halogen, a lower alkyl group including preferably 1 to 4 carbon atoms, an —OZ group, Z being a hydroxyalkyl, alkoxyalkyl, acylaminoalkyl, carbalkoxyaminoalkyl, mesylaminoalkyl, ureidoalkyl, aminoalkyl, mono- or dialkylaminoalkyl group.

In the preceding definition, halogen includes fluorine, bromine or preferably chlorine.

Particularly efficacious compounds to be used in the compositions according to the invention include: paraphenylene diamine, paratoluylene diamine, methoxy paraphenylene diamine, chloroparaphenylene diamine, dimethyl-2,6 paraphenylene diamine, dimethyl-2,5 paraphenylene diamine, methyl-2 methoxy-5 paraphenylene diamine, dimethyl-2,6 methoxy-5 paraphenylene diamine, N,N-dimethyl paraphenylene diamine, methyl-3 amino-4 N,N-(diethyl)aniline, mono- and di-(Beta-hydroxy ethyl) paraphenylene diamine, methyl-3 amino-4 N,N-di (Beta-hydroxyethyl) aniline, amino-4 N,N-(ethyl, carbamylmethyl) aniline, methyl-3 amino-4 N,N-(ethyl, carbamylmethyl) aniline, amino-4 N,N-(ethyl, morpholinoethyl) aniline, methyl-3 amino-4 N,N-(ethyl, morpholinoethyl) aniline, amino-4 N-(acetylaminoethyl) aniline, amino-4 N,N-(ethyl, acetylaminoethyl) aniline, chloro-3 amino-4 N,N-di (Beta-hydroxyethyl) aniline, amino-4 N,N(ethyl, mesylaminoethyl) aniline, methyl-3-amino-4 N,N-(ethyl, mesylaminoethyl) aniline, amino-4 N,N-(ethyl, Beta-sulfoethyl)aniline, methyl-3 amino-4 N,N-(ethyl, Beta-sulfoethyl)aniline, N-/(amino-4') phenyl/morpholine, N-/(amino-4')phenyl/piperidine, amino-4, N,N-(ethyl, piperidinoethyl)aniline, methyl-3 amino-4 N-methyl aniline, chloro-2 amino-4 N,N-(ethyl, sulfonamidomethyl) aniline, chloro2 amino-4 N-(ethyl)aniline, methyl-2 amino-4 N-(Beta-hydroxyethyl)aniline, (diamino-2,5)phenoxyethanol, Beta-methoxyethylamino-4 aniline, and methyl-3 amino-4 N,N-(ethyl, acetylaminoethyl)aniline.

The paraphenylenediamines can be used in the form of a free base or in the salt form, for instance, as the mono-, di- or tri-hydrochloride, hydrobromide, sulfate or tartrate.

Other oxidizing bases include paraaminophenol, methyl-2 amino-4 phenol, methyl-3 amino-4 phenol, chloro-2 amino-4 phenol, chloro-3 amino-4 phenol, dimethyl-2,6 amino-4 phenol, dimethyl-3,5 amino-4 phenol, dimethyl-2,3 amino-4 phenol, dimethyl-2,5 amino-4 phenol, diamino-2,5 pyridine, dimethylamino-2 amino-5 pyridine, diethyl-amino-2 amino-5 pyridine, methyl-2 amino-6 benzomorpholine, amino-5 indole, N-methylparaaminophenol, orthoaminophenol, paraaminodiphenylamine, orthophenylenediamines and their substitute derivatives.

The dye compositions which are the object of the present invention can contain couplers in addition to one or more oxidizing bases. The couplers which can be used in the compositions according to the invention are of the general formula:

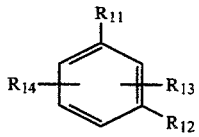

in which:
R$_{11}$ and R$_{12}$, identical or different, represent hydroxy, —NHR, where R can be hydrogen, acyl, ureido, carbalkoxy, carbamylalkyl, alkyl, dialkylcarbamylalkyl, hydroxyalkyl or mesylaminoalkyl group; R$_{11}$ and R$_{12}$ may also represent hydrogen or alkoxy or alkyl, so long as at least one of R$_{11}$ and R$_{12}$ represents OH (hydroxy);
R$_{13}$ and R$_{14}$ represent hydrogen, alkyl branched or linear, halogen, amino, alkylamino, acylamino, ureido, OZ, Z being a hydroxyalkyl, alkoxyalkyl, mesylaminoalkyl, acylaminoalkyl, ureidoalkyl or carbalkoxyalkyl group.

Specific couplers which correspond to the foregoing formula include resorcinol, metaaminophenol, diamino-2,4 anisole, methyl-2 ureido-5 phenol, dimethyl-2,6 aminophenol, methyl-2 acetylamino-5 phenol, dimethyl-2,6 acetylamino-5 phenol, amino-3 methoxy-4 phenol, methyl-2 N-Beta hydroxyethylamino-5 phenol, metaphenylene diamine, metatoluylene diamine, N-methyl meta aminophenol, methyl-6 amino-3 phenol, (diamino-2,4) phenoxyethanol, or a salt of these compounds.

Other couplers usable in the compositions of the invention are, for example: alphanaphthol, heterocyclic compounds such as, in particular, hydroxy-6 benzomorpholine, amino-6 benzomorpholine, pyridine derivatives such as diamino-2,6 pyridine, pyrazolones or diketonic compounds or their salts.

The diketonic compounds which are especially useful as couplers in the compositions according to the invention correspond to the formula:

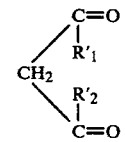

in which: R'$_1$ and R'$_2$ each represent independently alkyl (preferably lower alkyl having 1 to 4 carbon atoms), alkoxy, phenyl

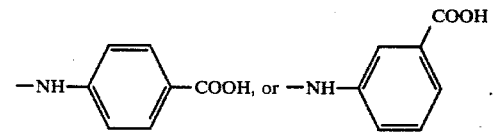

The pyrazolones useful as couplers, in the compositions of the invention, are preferably those corresponding to the formula:

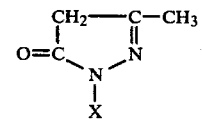

in which: X represents phenyl, unsubstituted or substituted by an —SO$_3$H group and/or by a halogen which is fluorine, bromine, or preferably chlorine.

Direct dyes can be added to the oxidation dyes used in the invention, such as azo dyes, anthraquinones, nitrated or nitro derivative of benzene, such as (nitro-3 methylamino-4) phenoxyethanol, 1-N-methylamino 2-nitro 4-N,N di-Beta-hydroethyl amino benzene, 1-Beta-hydroxyethylamino 2-methoxy 4-nitro benzene, or 3-nitro 4-Beta-hydroxyethylamino phenol, 1-methoxy 3-nitro 4-Beta-hydroxyethylamino benzene, (3-nitro 4-amino) phenoxy ethanol; indamines, indoanilines, indophenols, or other oxidation dyes such as the leuco derivatives of the three last compounds, polyphenols, aminodiphenols, polyaminophenols, such as hydroquinone, 1,2-dihydroxy benzene, 1,5-dihydroxy naphthalene, 1,2,4- or 1,3,5-trihydroxy benzene, 2,6-diamino 4-dimethylamino phenol.

Benzyl alcohol is used according to the invention in concentrations (before dilution) of from 2 to 20% by weight, and preferably 5 to 15% by weight.

The invention dye compositions contain an excess of an alkalizing agent, which is primarily, preferably, ammonia. This excess, necessary for the decoloring effect mentioned above, represents from 1 to 30%, and preferably 7 to 15% by weight of the total weight of the composition. It is defined in relation to the quantity necessary to make the soap.

The dye compositions of the invention can also contain various conventional adjuvants. These adjuvants can be solvents, fatty amides, fatty alcohols, natural or synthetic, natural or synthetic oxyethylenated or polyglycerolated alcohols, oxyethylenated alkyl phenols, alkaline sulfate alkoyls oxyethylenated or not, preservative agents, sequestering agents, antioxidizing agents or perfumes.

The dye compositions can contain 0 to 20% solvents; from 0 to 15% fatty amides, from 0 to 25% fatty alcohols, oxyethylenated or polyglycerolated fatty alcohols or oxyethylenated alkyl phenols, and from 0 to 15% alkyl sulfates, oxyethylenated or not. These concentrations are given by weight of the composition (prior to dilution).

Solvents which can be used in the compositions with the benzyl alcohol can be, for example, lower aliphatic alcohols such as ethyl alcohol, propyl or isopropyl alcohol, glycols such as propylene glycol, methylglycol, ethylglycol and butylglycol, diethyleneglycol, dipropyleneglycol, hexyleneglycol, or monoethylester diethyleneglycol.

These solvents or their mixtures are generally used in concentrations (before dilution) of from 2 to 20% and preferably from 5 to 15% by weight of the composition.

Preferred fatty amides include lauric or oleic diethanolamide, mono- or diethanolamide of copra, stearic monoethanolamide.

These amides are generally used in concentrations (before dilution) of from 0.5 to 15%, and preferably from 1 to 10% by weight of the composition.

Preferred natural or synthetic fatty alcohols include oleic, lauric, octyldodecyl, hexyldodecyl, hexyldecyl, isostearyl, myristic, cetyl, stearyl and hydroxystearyl alcohols.

These alcohols are generally used in concentrations (before dilution) of from 1 to 25%, and preferably from 5 to 15% by weight of the composition.

Preferred oxyethylenated or polyglycerolated natural or synthetic fatty alcohols and oxyethylenated alkylphenols, include oleic alcohol polyoxyethylenated with 10 to 30 moles of ethylene oxide, oxyethylenated lauric alcohol (12 moles of ethylene oxide), oxyethylenated cetyl alcohol (6 to 10 moles of ethylene oxide), oxyethylenated cetyl stearyl alcohol (10 moles of ethylene oxide), oleocetyl alcohol (30 moles of ethylene oxide), stearyl alcohol (10-15 or 20 moles of ethylene oxide), oleic alcohol polyglycerolated with 4 moles of glycerol, the polyoxyethylenated synthetic fatty alcohols $C_9$–$C_{15}$ (5 to 10 moles of ethylene oxide), nonylphenol oxyethylenated with 2 to 10 moles of ethylene oxide.

Said fatty alcohols or alkylphenols are generally used in concentrations (before dilution) of from 1 to 25%, and preferably from 2 to 20% by weight of the composition.

The alkyl sulfates, oxyethylenated or not, generally in the form of alkaline salts, include sodium lauryl sulfate, ammonium or triethanol-amine sulfate, sodium cetyl stearyl sulfate, triethanolamine cetyl stearyl sulfate, monoethanolamine lauryl sulfate, oxyethylenated sodium lauryl ester sulfate with for example 2.2 moles of ethylene oxide, oxyethylenated monoethanolamine lauryl ester sulfate with for example 2.2 moles of ethylene oxide. These sulfates are generally used in concentrations (before dilution) of from 0.5 to 15% and preferably 1 to 10% by weight.

The anti-oxidizing agents, which are present in a quantity sufficient to prevent premature oxidation of oxidizable components during storing of the composition, are for example sodium or potassium bisulfite, thioglycolic acid, hydroquinone, etc.

The vehicle or support according to the invention can be in the form, before dilution, of either a clear liquid or in the form of a cream.

According to the preferred production method for the invention, the support is in the form of a liquid. This liquid form is obtained by using one or several liquid fatty acids such as for example oleic acid or isostearic acid, possibly in a mixture with other fatty acids in proportions such that the mixture remains a liquid. Alkalization is effected preferably by ammonia and/or mono- or di-ethanolamine, the alkalizing agent being in excess of 1 to 30% as previously indicated. In a preferred production method for dilution of said liquid dye composition, the alkalizing agent is a mixture of ammonia and mono- or di-ethanolamine, the mono- or di-ethanolamine being in a stoichiometric quantity in relation to the fatty acid, and the ammonia being in sufficient quantity to obtain the lightening effect, i.e., preferably a quantity of ammonia of from 7 to 15% by weight in relation to the weight of the composition.

Of course, in compositions according to the preferred production method, the conventional adjuvants possibly present are the appropriate adjuvants for the production of liquid compositions.

According to this preferred production method, benzyl alcohol, present at a concentration of from 5 to 15%, is associated with at least one solvent previously cited, used at a concentration of from 2 to 20% and preferably 5 to 15%.

Preferred amides include oleic or lauric diethanolamide, mono- or diethanolamide of copra.

Preferred fatty acids include oleic, lauric, octyldodecyl, hexyldodecyl, hexyldecyl and isostearyl alcohols.

Surprisingly, it was discovered that a liquid vehicle of the invention, appearing as a clear liquid, gives, after dilution with oxygenated water used as diluent in a ratio of 1 to 2 and preferably 1, a mixture having the appearance and consistency of a cream and not a gel as might be expected.

The liquid support according to the invention provides for using gelatinizable liquids (which are gelatinized by admixture with the oxidizing agent) which also has the advantages of a cream once the mixture is prepared, that is, ease of application and good adherence to the hair.

Furthermore, the coloring qualities are excellent, combining the coverage qualities obtained with the cream supports to the qualities of transparence and shine obtained with the gel supports.

The pH of dye compositions of the invention may vary from 5 to 11, and preferably from 8 to 10.5.

The compositions of the invention are used for dyeing hair in the customary manner after the addition of an oxidizing agent.

The concentration of oxidizing base may vary from 0.001 to 10%, and preferably from 0.03 to 5% by weight, and that of the coupler may vary from 0.001 to 5%, and preferably from 0.015 to 2% by weight of the composition.

One part by weight of the dye composition may be mixed with 1 to 3 parts by weight of oxidizing agent.

The setting time may vary from 5 to 45 minutes and preferably from 15 to 30 minutes.

Another object of the invention is a hair dye composition which results from mixing the composition to be diluted such as previously defined and an excess of oxidizing solution.

The oxidizing solution is especially a solution of oxygenated water. By oxygenated water is meant hydrogen peroxide. It will be noted that a $H_2O_2$ solution having a concentration of n volumes is a solution which may give by decomposition n liters of oxygen, under normal conditions, by the reaction:

$$H_2O_2 \rightarrow H_2O_2 + \tfrac{1}{2}O_2.$$

Another object of the invention is a procedure for dyeing the hair characterized by the fact that such a dyeing composition is applied to the hair in sufficient quantity to obtain the desired tint.

The following examples illustrate the invention without, however, limiting it.

EXAMPLE 1

A dye carrier is prepared according to the invention in liquid form by mixing the following ingredients:
- Nonylphenol polyoxyethylenated with 9 moles of ethylene oxide—3 g
- Oleic alcohol—9 g
- Oleic diethanolamide—9 g
- Hydrogenated tallow amide with 50 moles of ethylene oxide—2.5 g
- Oleic acid—18 g
- Polymer A—3 g
- Ethyl alcohol (96%)—9 g
- Benzyl alcohol—11 g
- Ammonia, 22° Be—14 ml
- Monoethanolamine—6.5 g
- p-aminophenol base—0.2 g
- m-diamino anisol sulfate—0.1 g
- Resorcinol—0.5 g
- m-aminophenol base—0.2 g
- p-toluylene diamine—2 g
- Ethylene diamine tetracetic acid sold under the name Trilon B—0.2 g
- Sodium bisulfite (d=1.32)—1.2 g
- Hydroquinone—0.15 g
- Water, q.s.p.—100 g In a bowl, 30 g of this support are mixed with 30 g oxygenated water (concentration: 20 volumes). A gelatinized cream is obtained, stable, pleasant to apply and which adheres well to the hair.

It is applied with a brush. It is allowed to set 30 to 40 minutes and then is rinsed.

The hair is easily untangled. It is silky to the touch. The hair is set and then dried.

The hair is shiny, strong; it has body; it is silky to the touch and easy to untangle.

A dark chestnut shade is obtained.

Polymer A corresponds to the formula 1 in which: A is —$(CH_2)_3$—; B is —$(CH_2)_6$—; each of $R_1$, $R_2$, $R_3$ and $R_4$ is $CH_3$ and $X^-$ is $Br^-$.

EXAMPLE 2

A dye carrier according to the invention is prepared in liquid form by mixing the following ingredients:
- Triethanolamine lauryl sulfate with 40% active matter—4 g
- 2-octyl dodecanol marketed under the name EUTANOL G by the Henkel Company—11 g
- Oleic diethanolamide—8 g
- Oleocetyl alcohol with 30 moles of ethylene oxide marketed under the name MERGITAL OC 30 by the Henkel Company—3 g
- Oleic acid—21 g
- Polymer B—2 g
- Benzyl alcohol—12 g
- Ethyl alcohol (96%)—8 g
- Ammonia, 22° Be—19 ml
- p-aminophenol base—0.30 g
- Resorcinol—0.65 g
- m-aminophenol base—0.65 g
- p-toluylene diamine—0.15 g
- Ethylene diamine tetracetic acid sold under the name Trilon B—0.2 g
- Sodium bisulfite (d=1.32)—1.2 g
- Water, q.s.p.—100 g The procedures are undertaken as in Example 1. The results are the same as in Example 1, but a light golden blonde shade is obtained.

Polymer B is a compound of formula 1 in which: A is —$(CH_2)_3$—; B is —$(CH_2)_6$—; each of $R_1$, $R_2$, $R_3$ and $R_4$ is methyl and $X^-$ is $Cl^-$.

EXAMPLE 3

A dye carrier according to the invention in liquid form is prepared by mixing the following ingredients:
- Triethanolamine lauryl sulfate with 40% active matter—4.5 g
- Oleic alcohol—8 g
- Oleic diethanolamide—10 g
- Oleocetyl alcohol with 30 moles of ethylene oxide marketed under the name MERGITAL OC 30 by the Henkel Company—4 g
- Oleic acid—17 g
- Polymer C—3.5 g
- Benzyl alcohol—8 g
- Ethyl alcohol (96%)—10 g
- Ammonia, 22° Be—9 ml
- Monoethanolamine—7 g
- p-aminophenol base—0.70 g
- m-amino anisol sulfate—0.15 g
- Resorcinol—0.15 g
- m-aminophenol base—0.15 g
- Nitro p-phenylene diamine—0.015 g
- p-toluylene diamine—0.30 g
- Ethylene diamine tetracetic sold under the name Trilon B—0.2 g
- Sodium bisulfite (d=1.32)—1.2 g
- Water, q.s.p.—100 g The dye carrier is prepared as in Example 1; the results are the same, but a light golden chestnut shade is obtained.

Polymer C is a compound of formula I in which: A is —$(CH_2)_6$—; B is —$(CH_2)_3$—; each of $R_1$, $R_2$, $R_3$ and $R_4$ is $CH_3$ and $X^-$ is $Br^-$.

EXAMPLE 4

A dye support according to the invention is prepared in liquid form by mixing the following ingredients:
- Triethanolamine lauryl sulfate with 40% active matter—3.5 g
- 2-octyl dodecanol marketed under the name EUTANOL G by the Henkel Company—7 g
- Diethanolamide of coconut fatty acid marketed under the name COMPERLAN KD by the Henkel Company—8 g Oleocetyl alcohol with 30 moles ethylene oxide marketed under the name MERGITAL OC 30 by the Henkel Company—3 g
Oleic acid—19 g
Polymer D—4 g
Benzyl alcohol—10.5 g
Ethyl alcohol (96%)—9.5 g
Ammonia, 22° Be—19.5 ml
p-aminophenol base—0.22 g
m-diamino anisol sulfate—0.044 g
Resorcinol—0.12 g
m-aminophenol base—0.075 g
Nitro-p-phenylene diamine—0.030 g
p-toluylene diamine—0.16 g
Ethylene diamine tetracetic acid sold under the name Trilon B—0.2 g
Sodium bisulfite (d=1.32)—1.2 g
Water, q.s.p.—100 g Procedures are undertaken as in Example 1 with the same results but a coppery light blonde shade is obtained.

Polymer D is a compound of formula I in which: A is —$(CH_2)_6$—; B is —$(CH_2)_4$—; each of $R_1$, $R_2$, $R_3$ and $R_4$ is $CH_3$ and $X^-$ is $Br^-$.

EXAMPLE 5

A dye carrier according to the invention is prepared in liquid form by mixing the following ingredients:
Triethanolamine lauryl sulfate with 40% active matter—3 g
2-octyl dodecanol marketed under the name EUTANOL G by the Henkel Company—8 g
Oleic diethanolamide—6 g
Hydrogenated tallow amide with 50 moles ethylene oxide—3.5 g
Oleic acid—18 g
Polymer E—3 g
Benzyl alcohol—9 g
Ethyl alcohol (96%)—10 g
Monoethanolamine—6 g
Ammonia, 22° Be—10 ml
p-aminophenol base—0.060 g
m-diamino anisol sulfate—0.02 g
Resorcinol—0.25 g
m-aminophenol base—0.08 g
p-toluylene diamine—0.60 g
Ethylene diamine tetracetic acid sold under the name Trilon B—0.2 g
Sodium bisulfite (d=1.32)—1.2 g
Water, q.s.p.—100 g The procedures are undertaken as in Example 1, with the same results, but a blonde shade is obtained.

Polymer E is a compound of formula I in which: A is —$(CH_2)_2$—; B is —$(CH_2)_4$—; each of $R_1$, $R_2$, $R_3$ and $R_4$ is $CH_3$ and $X^-$ is $Br^-$.

EXAMPLE 6

A dye carrier according to the invention is prepared in liquid form by mixing the following ingredients:
2-octyl dodecanol marketed under the name EUTANOL G by the Henkel Company—12 g
Oleic diethanolamide—9 g
Oleocetyl alcohol with 30 moles ethylene oxide marketed under the name MERGITAL OC 30 by the Henkel Company—2 g
Oleic acid—20 g
Polymer F—1.5 g
Benzyl alcohol—11 g
Ethyl alcohol (96%)—11 g
Ammonia, 22° Be—17.5 ml
p-aminophenol base—0.08 g
m-diamino anisol sulfate—0.04 g
Resorcinol—0.248 g
m-aminophenol base—0.07 g
Nitro p-phenylene diamine—0.002 g
p-toluylene diamine—0.3 g
Ethylene diamine tetracetic acid sold under the name Trilon B—0.2 g
Sodium bisulfite (d=1.32)—1.2 g
Water, q.s.p.—100 g The procedures are as in Example 1; the results are the same, but an ash-blonde shade is obtained.

Polymer F is a compound of formula I in which: A is —$(CH_2)_6$—; B is —$(CH_2)_5$—; each of $R_1$, $R_2$, $R_3$ and $R_4$ is $CH_3$ and $X^-$ is $Br^-$.

EXAMPLE 7

A dye carrier according to the invention is prepared in liquid form by mixing the following ingredients:
Triethanolamine lauryl sulfate with 40% active matter—3 g
2-octyldodecanol marketed under the name EUTANOL G by the Henkel Company—10 g
Oleic diethanolamide—10 g
Oleic acid—19 g
Polymer G—2.5 g
Benzyl alcohol—10 g
Ethyl alcohol (96%)—10 g
Ammonia, 22° Be—12.5 ml
Monoethanolamine—7 g
p-aminophenol base—0.09 g
Resorcinol—0.09 g
m-aminophenol base—0.04 g
p-toluylene diamine—0.08 g
Ethylene diamine tetracetic acid sold under the name Trilon B—0.2 g
Sodium bisulfite (d=1.32)—1.2 g
Water, q.s.p.—100 g The procedures are as in Example 1; the results are the same but a very light blond shade is obtained.

Polymer G is a compound of formula I in which: A is —$(CH_2)_3$—; B is —$(CH_2)_4$—; each of $R_1$, $R_2$, $R_3$ and $R_4$ is $CH_3$ and $X^-$ is $Br^-$.

EXAMPLE 8

A dye carrier according to the invention is prepared in liquid form by mixing the following ingredients:
Triethanolamine lauryl sulfate with 40% active matter—4 g
2-octyldodecanol marketed under the name EUTANOL G by the Henkel Company—11 g
Oleic diethanolamide—8 g
Oleocetyl alcohol with 30 moles ethylene oxide marketed under the name MERGITAL OC 30 by the Henkel Company—3 g
Oleic acid—21 g
Polymer B—2 g
Benzyl alcohol—12 g
Ethyl alcohol (96%)—8 g
Ammonia, 22° Be—19 ml
Amino-1(methoxy-2 ethyl)amino-4-benzene dihydrochloride—0.4 g
p-aminophenol base—0.25 g
Resorcinol—0.07 g
m-aminophenol base—0.04 g
N(2-hydroxyethyl)amino-5 methyl-2 phenol—0.12 g (Hydroxy-2 ethyloxy)-1 diamino-2,4 benzene dihydrochloride—0.03 g
Methoxy-1 nitro-3 beta hydroxyethylamino-4 benzene—0.07 g
Beta hydroxyethyloxy-1 nitro-3 amino-4 benzene—0.06 g
Hydroquinone—0.1 g
Ethylene diamine tetracetic acid sold under the name Trilon B—0.24 g
Sodium bisulfite (d=1.32)—1 ml
Water, q.s.p.—100 g The procedure is as in Example 1; the results are the same, but a light blonde shade is obtained.

EXAMPLE 9

A dye carrier according to the invention is prepared in liquid form by mixing the following ingredients:
Lauryl sulfate of triethanolamine with 40% active matter—4.5 g
Oleic alcohol—8 g
Oleic diethanolamide—10 g
Oleocetyl alcohol with 30 moles ethylene oxide marketed under the name MERGITAL OC 30 by the Henkel Company—4 g
Oleic acid—17 g
Polymer C—3.5 g
Benzyl alcohol—8 g
Ethyl alcohol (96%)—10 g
Ammonia, 22° Be—9 ml
Monoethanolamine—7 g
Amino-1 (methoxy-2 ethyl)amino-4 benzene dihydrochloride—0.18 g
p-aminophenol base—0.4 g
Resorcinol—0.03 g
m-aminophenol base—0.04 g
(diamino-2,4) phenoxyethanol dihydrochloride—0.02 g
Methoxy-1 nitro-3 beta hydroxyethylamino-4 benzene—0.52 g
(Nitro-3 amino-4) phenoxyethanol—0.1 g
Hydroquinone—0.1 g
Ethylene diamine tetracetic acid sold under the name Trilon B—0.24 g
Sodium bisulfite (d=1.32)—1 ml
1-phenyl 3-methyl 5-pyrazolone—0.2 g
Water, q.s.p.—100 g The preparation is as in Example 1; the results are the same, but a golden blonde shade is obtained.

EXAMPLE 10

A dye carrier according to the invention is prepared in liquid form by mixing the following ingredients:
2-octyldodecanol marketed under the name EUTANOL G by the Henkel Company—12 g
Oleic diethanolamide—9 g
Oleocetyl alcohol with 30 moles ethylene oxide marketed under the name of MERGITAL OC 30 by the Henkel Company—2 g
Oleic acid—20 g
Polymer F—1.5 g
Benzyl alcohol—11 g
Ethyl alcohol (96%)—11 g
Ammonia, 22° Be—17.5 ml
N,N-bis(2-hydroxyethyl) paraphenylene diamine sulfate—1 g
p-aminophenol base—0.4 g
Resorcinol—0.15 g
m-aminophenol base—0.1 g
Alphanaphthol—0.4 g
Hydroquinone—0.1 g
Ethylene diamine tetracetic acid—0.24 g
Sodium bisulfite (d=1.32)—1 ml
Water, q.s.p.—100 g The composition was formed in accordance with the procedures set forth in Example 1. The resulting dye shade was a dark ash blonde.

EXAMPLE 11

A dye composition according to the invention is prepared in liquid form by mixing the following ingredients:
Triethanolamine lauryl sulfate with 40% active matter—2 g
2-octyldodecanol marketed under the name EUTANOL G by the Henkel Company—11 g
Oleic diethanolamide—10.5 g
Oleic acid—18 g
Polymer H—2.3 g
Benzyl alcohol—8 g
Propylene glycol—8 g
Ethyl alcohol (96%)—6 g
Ammonia, 22° Be—13.5 ml
Monoethanolamine—4 g
p-aminophenol base—0.30 g
Resorcinol—0.65 g
m-aminophenol base—0.65 g
p-toluylene diamine—0.15 g
Ethylene diamine tetracetic acid sold under the name Trilon B—0.2 g
Sodium bisulfite (d=1.32)—1.2 g
Water, q.s.p.—100 g The composition is prepared as in Example 1; the results are the same; but a light golden blonde shade is obtained.

Polymer H is a compound of formula I in which: A is —(CH$_2$)$_3$—; B is —(CH$_2$)$_5$—; each of R$_1$, R$_2$, R$_3$ and R$_4$ is CH$_3$ and X$^-$ is Br$^-$.

EXAMPLE 12

A dye composition according to the invention is prepared in liquid form by mixing the following ingredients:
Triethanolamine lauryl sulfate with 40% active matter—5 g
2-octyldodecanol marketed under the name EUTANOL G by the Henkel Company—8 g
Diethanolamide of coconut fatty acid marketed under the name COMPERLAN KD by the Henkel Company—9 g
Stearyl alcohol with 20 moles of ethylene oxide sold under the name Brij 78—2.5 g
Oleic acid—22 g
Polymer I—3.2 g
Benzyl alcohol—10 g
Ethyl alcohol (96%)—6 g
Ethyl glycol—4 g
Ammonia, 22° Be—18 ml
p-aminophenol base—0.70 g
m-diamino anisol sulfate—0.15 g
Resorcinol—0.15 g
m-aminophenol base—0.15 g
Nitro p-phenylene diamine—0.015 g
p-toluylene diamine—0.30 g
Ethylene diamine tetracetic acid sold under the name Trilon B—0.2 g
Sodium bisulfite (d=1.32)—1.2 g Water, q.s.p.—100 g The composition was prepared as in Example 1; the results are the same, but a light golden chestnut shade is obtained.

Polymer I is a compound of formula I in which: A is —($CH_2$)$_2$—; B is —($CH_2$)$_5$—; each of $R_1$, $R_2$, $R_3$ and $R_4$ is $CH_3$ and $X^-$ and $Br^-$.

EXAMPLE 13

A dye carrier according to the invention is prepared in liquid form by mixing the following ingredients:

Nonylphenol with 9 moles ethylene oxide—4 g
Oleic alcohol—8.5 g
Oleic diethanolamide—9.5 g
Hydrogenated tallow amide with 50 moles ethylene oxide—2 g
Oleic acid—18.5 g
Polymer J—1.8 g
Ethyl alcohol (96%)—6 g
Benzyl alcohol—8 g
Ammonia, 22° Be—12 ml
Monoethanolamine—7 g
Butyl glycol—4 g
N,N-bis (2-hydroxyethyl) paraphenylene diamine sulfate—1 g
p-aminophenol base—0.4 g
Resorcinol—0.15 g
m-aminophenol base—0.1 g
Alphanaphthol—0.4 g
Hydroquinone—0.1 g
Ethylene diamine tetracetic acid sold under the name of Trilon B—0.24 g
Sodium bisulfite (d=1.32)—1 ml
1-phenyl 3-methyl 5-pyrazolone—0.2 g
Water, q.s.p.—100 g The composition is prepared as in Example 1; the results are the same, but a dark ash blonde shade is obtained.

Polymer J is a compound of formula I in which: A is —($CH_2$)$_2$—O—($CH_2$)$_2$—; B is —$CH_2$—CHOH—$CH_2$—; each of $R_1$, $R_2$, $R_3$ and $R_4$ is $CH_3$ and $X^-$ is $Br^-$.

EXAMPLE 14

A dye composition according to the invention is prepared in cream form by mixing the following ingredients:

Stearyl cetyl alcohol—19 g
2-octyl dodecanol marketed under the name EUTANOL G by the Henkel Company—4.5 g
Stearyl alcohol with 15 moles ethylene oxide—2.5 g
Ammonium lauryl sulfate with 30% active matter—12 g
Polymer L—4 g
Benzyl alcohol—2 g
Ammonia, 22° Be—11 ml
Resorcinol—0.420 g
Meta aminophenol—0.150 g
m-diamino anisole sulfite—0.048 g
p-nitro phenylene diamine—0.085 g
p-toluylene diamine—0.004 g
Ethylene diamine tetracetic acid marketed under the name Trilon B—1.000 g
Sodium bisulfite (d=1.3)—1.200 g
Water, q.s.p.—100 g 30 g of this composition are mixed in a bowl with 45 g oxygenated water (20 volumes). A smooth cream is obtained, pleasant to apply and which adheres well to the hair. This cream is applied to the hair with a brush. The hair is allowed to set 30 minutes and rinsed.

The hair is easily untangled and silky to the touch. The hair is set and dried.

The hair is shiny, strong and has body, it is silky to the touch and easy to untangle.

On 100% white hair, a blonde shade is obtained.

Polymer L is a compound of formula I in which:

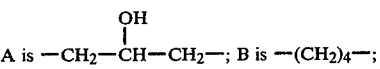

A is —$CH_2$—CH—$CH_2$—; B is —($CH_2$)$_4$—;

each of $R_1$, $R_2$, $R_3$ and $R_4$ is $CH_3$ and $X^-$ is $Br^-$.

EXAMPLE 15

A dye composition according to the invention is prepared in liquid form by mixing the following ingredients:

Oleic acid—4.3 g
Monoethanolamine—0.95 g
Cetylstearyl alcohol—16 g
Oleic alcohol—5 g
Mergital OC 30—2.8 g
Polymer K—4 g
Benzyl alcohol—2.2 g
Ammonia, 22° Be—11 ml
Resorcine—0.420 g
Metaaminophenol—0.150 g
m-diaminoanisole sulfate—0.048 g
p-nitrophenylene diamine—0.085 g
p-toluylene diamine—0.004 g
Trilon B—1.000 g
Sodium bisulfite d=1,3—1.200 g
Water qsp—100 g The composition is mixed with an appropriate amount of $H_2O_2$ solution (concentration: 20 volumes). A cream is obtained, which is applied on hair as described in the preceding examples. A blonde shade is obtained.

Polymer K is a compound of formula I in which: A is —($CH_2$)$_6$—; B is —($CH_2$)$_2$—O—($CH_2$)$_2$—; each of $R_1$, $R_2$, $R_3$ and $R_4$ is $CH_3$ and $X^-$ is $Cl^-$.

EXAMPLE 16

A dye composition in liquid form is prepared by mixing the following ingredients:

Nonylphenol polyoxethylenated with 9 moles ethylene oxide—3 g
Oleic alcohol—9 g
Oleic diethanolamide—9 g
Hydrogenated tallow amide polyoxyethylenated with 50 moles ethylene oxide—2.5 g
Oleic acid—18 g
Polymer $P_1$—3 g
Ethyl alcohol (96%)—9 g
Benzyl alcohol—11 g
Ammonia, 22° Be—14 ml
Monoethanolamine—6.5 g
p-aminophenol—0.2 g
m-diamino anisole sulfate—0.1 g
Resorcinol—0.5 g
m-aminophenol—0.2 g
p-toluylene diamine—2 g
Ethylene diamine tetracetic acid sold under the name Trilon B—0.2 g
Sodium bisulfite (d=1.32)—1.2 g Water, q.s.p.—100 g In a bowl 30 g of this support are mixed with 30 g oxygenated water (20 volumes). A gelatinized cream is obtained, consistent, easy to apply and which adheres well to the hair.

It is applied with a brush. It is allowed to set 30 to 40 minutes and rinsed.

The hair untangles easily. It is silky to the touch.

The hair is shiny, strong, and has body (volume); it is silky to the touch and easy to untangle.

A dark chestnut shade is obtained.

The $P_1$ polymer is described below in Preparation No. 5.

EXAMPLE 17

A dye composition in liquid form is prepared by mixing the following ingredients:

Triethanolamine lauryl sulfate with 40% active matter—4.5 g
Oleic alcohol—8 g
Oleic diethanolamide—10 g
Oleocetyl alcohol with 30 moles ethylene oxide marketed under the name MERGITAL OC 30 by the Henkel Company—4 g
Oleic acid—17 g
Polymer $P_5$—3.5 g
Benzyl alcohol—8 g
Ethyl alcohol (96%)—10 g
Ammonia, 22° Be—9 ml
Monoethanolamine—7 g
p-aminophenol—0.70 g
m-diamino anisole sulfate—0.15 g
Resorcinol—0.15 g
m-aminophenol—0.15 g
Nitro p-phenylene diamine—0.015 g
p-toluylene diamine—0.30 g
Ethylene diamine tetracetic acid sold under the name Trilon B—0.2 g
Sodium bisulfite (d=1.32)—1.2 g
Water, q.s.p.—100 g The composition is prepared as in Example 16; the results are the same, but a light golden chestnut shade is obtained.

Comparable results have been obtained by replacing the $P_5$ polymer with an equivalent amount of the $P_2$ or $P_4$ polymer, or a mixture of the $P_2$ and $P_4$ polymers.

The polymers $P_2$, $P_5$, and $P_4$ are described below in Preparation Nos. 1, 2 and 3.

EXAMPLE 18

A dye composition in liquid form is prepared by mixing the following ingredients:

Triethanolamine lauryl sulfate with 40% active matter—4 g
2-octyldodecanol marketed under the name EUTANOL G by the Henkel Company—11 g
Oleic diethanolamide—8 g
Oleocetyl alcohol with 30 moles ethylene oxide marketed under the name MERGITAL OC 30 by the Henkel Company—3 g
Oleic acid—21 g
Polymer $P_2$—2 g
Benzyl alcohol—12 g
Ethyl alcohol (96%)—8 g
Ammonia, 22° Be—19 ml
1-(Beta-methoxy-ethyl)amino-4 aniline dihydrochloride—0.4 g
p-aminophenol—0.25 g
Resorcinol—0.07 g
m-aminophenol—0.04 g
N(Beta-hydroxyethyl)amino-5 methyl-2 phenol—0.12 g
(diamino-2,4)phenoxyethanol dihydrochloride—0.03 g
Hydroquinone—0.1 g
Ethylene diamine tetracetic acid sold under the name Trilon B—0.24 g
Sodium bisulfite (d=1.32)—1 ml
Water, q.s.p.—100 g The composition is prepared as in Example 16; the results are the same, but a light blonde shade is obtained.

Comparable results have been obtained by replacing the $P_2$ polymer with an equivalent quantity of the $P_3$ or $P_5$ polymer.

Polymer $P_5$ is described below in Preparation No. 1.

EXAMPLE 19

A dye composition in liquid form is prepared by mixing the following ingredients:

Nonylphenol with 9 moles ethylene oxide—4 g
Oleic alcohol—8.5 g
Oleic diethanolamide—9.5 g
Hydrogenated tallow amide polyoxyethylenated with 50 moles of ethylene oxide—2 g
Oleic acid—18.5 g
Polymer $P_4$—1.8 g
Ethyl alcohol (96%)—6 g
Benzyl alcohol—8 g
Ammonia, 22° Be—12 ml
Monoethanolamine—7 g
Butyl glycol—4 g
N,N-bis(Beta-hydroxyethyl) paraphenylene diamine sulfate—1 g
p-aminophenol—0.4 g
Resorcinol—0.15 g
m-aminophenol—0.1 g
Alphanaphthol—0.4 g
Hydroquinone—0.1 g
Ethylene diamine tetracetic acid sold under the name Trilon B—0.24 g
Sodium bisulfite (d=1.32)—1 ml
1-phenyl 3-methyl 5-pyrazolone—0.2 g
Water, q.s.p.—100 g The composition is prepared as in Example 16, the results are the same, but a dark ash blonde shade are obtained.

Comparable results have been obtained by replacing the $P_4$ polymer with an equivalent quantity of the $P_2$ or $P_5$ polymer.

EXAMPLE 20

A dye composition containing the following ingredients is prepared:

Oleic acid—4 g
Monoethanolamine—0.93 g
Cetyl stearyl alcohol—15 g
Oleic alcohol—5 g
MASQUOL DTPA—2 g
Oleocetyl alcohol with 30 moles ethylene oxide—3 g
Polymer $P_5$—3 g
Ammonia, 22° Be—13 ml
Benzyl alcohol—2 g
Resorcinol—0.2 g
m-aminophenol—0.25 g
N-(Beta-hydroxyethyl)amino-5 methyl-2 phenol—0.02 g Diamino-2,4 phenoxyethanol dihydrochloride—0.02 g
Sodium bisulfite (d=1.32)—1 ml
Water, q.s.p.—100 g 30 g of this composition are mixed with 45 g oxygenated water (20 volumes).

A cream is obtained which is applied to the hair with a brush and allowed to rest 30 minutes and then rinsed.

On 100% white hair a light chestnut shade is obtained.

Comparable results have been obtained by replacing the $P_5$ polymer with an equivalent quantity of the $P_2$ polymer or with a mixture of the $P_2$ and $P_3$ polymers.

The methods for preparation of the $P_1$–$P_5$ cationic polymers used in the examples, for producing the compositions are set forth below.

Preparation No. 1

Preparation of the $P_5$ polymer having the repeating units:

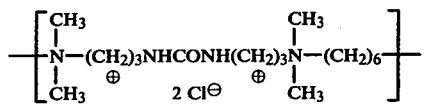

With vigorous agitation 46 g (0.2 mole) of N,N'-bis(-dimethyl-amino-3 propyl)-urea, 31 g (0.2 mole) dichloro-1,6 hexane and 50 g water are heated under reflux for 3 hours; cooled; and then 140 g water are added to the viscous solution thus obtained. About 150 g water are distilled so as to eliminate traces of residual dichloro-1,6 hexane. Then the solution's concentration is adjusted to 50% of the polymer obtained.

| Analysis of solution | Calculated Cl⊖: | 9.22% |
|---|---|---|
| at 50% | Found Cl⊖: | 8.68% |

Appearance: viscous solution, clear, colorless.

Preparation No. 2

Preparation of the $P_2$ polymer having repeating units:

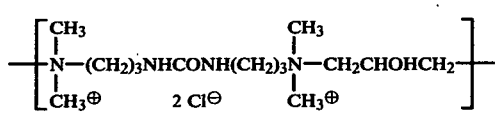

The same operational method as for Preparation No. 1 was used but employing N,N'-bis-(dimethylamino-3 propyl)-urea and dichloro-1,3 propanol-2.

| Analysis of solution | Calculated Cl⊖: | 9.89% |
|---|---|---|
| at 50% | Found Cl⊖: | 8.78% |

Appearance: viscous solution, clear, colorless.

Preparation No. 3

Preparation of the $P_4$ polymer having the following repeating units:

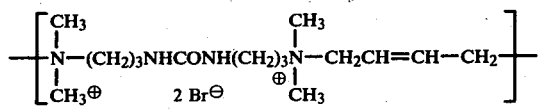

This compound is prepared according to the same operational method used to prepare polymer $P_5$ but N,N'-bis(dimethylamino-3 propyl)-urea and trans dibromo-1-butene-2 were employed.

| Analysis of solution | Calculated Br⊖: | 18% |
|---|---|---|
| at 50% | Found Br⊖: | 17.32% |

Appearance: viscous solution, slightly yellow, clear.

Preparation No. 4

Preparation of the $P_3$ polymer having the following repeating units:

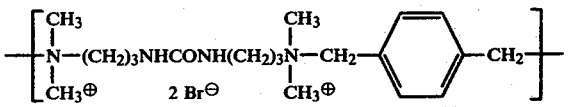

With vigorous agitation 46 g (0.2 mole) of N,N'-bis(-dimethylamino-3 propyl)-urea, 52.8 g (0.2 mole) of bis(-bromomethyl)-1,4 benzene and 216 g of methanol were heated in a 500 cm³ erlen for 3 hours. After cooling, methanol is distilled under reduced pressure, 200 cm³ of water are added; the aqueous phase is washed three times with 100 cm³ chloroform.

150 cm³ of water were removed by distillation under reduced pressure, and the concentration of the solution obtained was adjusted to 50% active matter by dilution with water.

| Analysis of solution | Calculated Br⊖: | 16.2% |
|---|---|---|
| at 50% | Found Br⊖: | 14.7% |

Appearance: viscous solution, clear, colorless.

Preparation No. 5

Preparation of the $P_1$ polymer having the following repeating units:

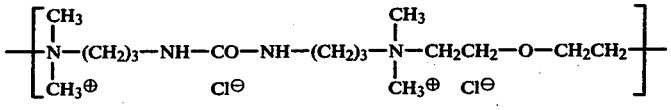

46 g (0.2 mole) N,N'-bis(dimethylamino-3 propyl)-urea and 50 g water are mixed and heated to about 50°–60° C.; 28.6 g (0.2 mole) of Beta, Beta'-dichloroethyl ester are introduced and heating is continued under reflux for 11 hours. Then 140 cm³ of water are added. The water is distilled therefrom until a 50% active matter solution is obtained.

| Analysis of solution | Calculated Cl⁻: | 9.5% |
| at 50% | Found Cl⁻: | 9.19% |

EXAMPLE 21

The following liquid dye composition was prepared:
Isostearic acid—4 g
Monoethanolamine—0.93 g
Cetylstearyl alcohol—20 g
Oleic alcohol—4 g
Mergital OC 30—4 g
Polymer K—5 g
Benzyl alcohol—2.5 g
Ammonia, 22° Be—11 ml
1-amino 4-(2-methoxy ethyl) amino benzene, dihydrochloride—1.6 g
p-aminophenol—0.3 g
Resorcine—0.2 g
m-aminophenol—0.25 g
N-(2-hydroxyethyl)5-amino 2-methyl phenol—0.02 g
1-2-(hydroxy ethyloxy) 2,4-diamino benzene, dihydrochloride—0.02 g
Trilon B—0.20 g
Thioglycolic acid—0.20 g
Water, qsp—100 g By mixing with an appropriate amount of $H_2O_2$, there is obtained a cream which is applied on hair as previously described and gives a light chestnut shade.

Polymer K is a compound of formula I wherein: $A = -(CH_2)_6-$; $B = -(CH_2)_2-O-(CH_2)_2-$; $R_1 = R_2 = R_3 = R_4 = CH_3$ and $X = Cl$.

EXAMPLE 22

The following liquid dye composition was prepared:
Triethanolamine laurylsulfate (40% active material)—3.5 g
Eutanol G—6 g
Oleic diethanolamide—11 g
Mergital OC 30—4 g
Oleic acid—17 g
Butylglycol—1 g
Ethyl alcohol (96%)—5.5 g
Benzyl alcohol—12 g
Polymer M—4 g
Ammonia, 22° Be—16 ml
p-toluylene diamine—1.5 g
p-aminophenol—0.21 g
1-(2-hydroxy ethyloxy) 2,4-diamino benzene, dihydrochloride—0.13 g
Resorcine—0.5 g
m-aminophenol—0.2 g
N-(2-hydroxyethyl)5-amino 2-methyl phenol—0.01 g
Trilon B—0.25 g
Sodium bisulfite (d=1.32)—1.2 g
Hydroquinone—0.15 g
1-phenyl 3-methyl 5-pyrazolone—0.17 g
Water, qsp—100 g By using similar procedures as in previous examples, there is obtained a dark chestnut shade.

Polymer M is a polymer of formula I with $A = (CH_2)_3$, $B = (CH_2)_4$, $R_1 = R_2 = R_3 = CH_3$, $R_4 = C_4H_9$ and $X = Br$.

EXAMPLE 23

The following liquid dye composition was prepared:
Nonylphenol polyoxyethylenated with 9 moles of ethylene oxide—3.5 g
Eutanol G—7 g
Diethanolamide of cocoanut oil acid sold under trade name Komperlan KD by Henkel—9 g
Mergital OC 30—3 g
Oleic acid—19 g
Monoethanolamine—7 g
Ethyl alcohol—3 g
Propylene glycol—2 g
Benzyl alcohol—15 g
Polymer N—3 g
Ammonia, 22° Be—10 ml
p-toluylene diamine—0.78 g
Resorcine—0.4 g
2-methyl 5-methoxy paraphenylene diamine—0.03 g
6-hydroxy benzomorpholine—0.02 g
p-aminophenol—0.18 g
1-(2-hydroxy ethyloxy) 2,4-diamino benzene, dihydrochloride—0.07 g
Trilon B—0.25 g
Hydroquinone—0.13 g
m-aminophenol—0.07 g
Sodium bisulfite (d=1.32)—1.1 g
1-phenyl 3-methyl 5-pyrazolone—0.18 g
Water, qsp—100 g By using similar procedures as in previous examples, there is obtained a chestnut shade.

Polymer N has units of formula I wherein $A = (CH_2)_3$, $B = (CH_2)_4$, $R_1 = R_2 = R_4 = CH_3$, $R_3 = C_3H_7$ and $X = Br$.

EXAMPLE 24

The following liquid dye composition was prepared:
Triethanolamine laurylsulfate (40% active material)—5.5 g
Oleic alcohol—8 g
Oleic diethanolamide—6 g
Amide of hydrogenated tallow, polyoxyethylenated with 50 moles of ethylene oxide—3.2 g
Oleic acid—18 g
Monoethanolamine—6 g
Ethyl alcohol—8 g
Benzyl alcohol—8 g
Polymer O—5.5 g
Ammonia, 22° Be—11 ml
p-aminophenol—0.19 g
m.diaminoanisole sulfate—0.1 g
Resorcine—0.6 g
m-aminophenol—0.21 g
p-toluylene diamine—1.8 g
Trilon B—0.3 g
Sodium bisulfite (d=1.32)—1.3 g
Hydroquinone—0.15 g
1-phenyl 3-methyl 5-pyrazolone—0.2 g
Water, qsp—100 g By using similar procedures as in previous examples, there is obtained a dark chestnut shade.

Polymer O consists of units of formula I wherein $A = (CH_2)_3$, $B = (CH_2)_4$, $R_1 = R_3 = CH_3$, $R_2 = R_4 = C_4H_9$ and $X = Br$.

EXAMPLE 25

The following liquid dye composition was prepared:
Nonylphenol, polyoxyethylenated with 9 moles of ethylene oxide—3 g
Eutanol G—10 g
Oleic diethanolamide—7.5 g Stearyl alcohol oxyethylenated with 20 moles of ethylene oxide, sold under tradename Brij 78 by Atlas—3 g
Oleic acid—19 g
Ethyl alcohol—11.5 g
Benzyl alcohol—7 g
Polymer Q—3.8 g
Ammonia, 22° Be—15 ml
p-toluylene diamine—0.8 g
p-aminophenol—0.14 g
2-methyl 5-methoxy paraphenylene diamine—0.028 g
m-diaminoanisole sulfate—0.05 g
Resorcine—0.36 g
m-aminophenol—0.078 g
6-hydroxy benzomorpholine—0.024 g
Hydroquinone—0.15 g
Trilon B—0.28 g
Sodium bisulfite (d=1.32)—1.2 g
1-phenyl 3-methyl 5-pyrazolone—0.18 g
Water qsp—100 g By using similar procedures as in previous examples, there is obtained a light chestnut shade.

Polymer Q consists of units of formula I wherein $A=(CH_2)_3$, $B=(CH_2)_6$, $R_1=R_3=C_2H_5$, $R_2=R_4=CH_3$, and $X=Br$.

EXAMPLE 26

The following liquid dye composition was prepared:
Triethanolamine laurylsulfate (40% active material)—4 g
Oleic alcohol—10 g
Komperlan KD—7 g
Mergital OC.30—2.5 g
Oleic acid—16 g
Monoethanolamine—6 g
Ethyl alcohol—7 g
Benzyl alcohol—11 g
Polymer R—3.5 g
Ammonia, 22° Be—12 ml
p-aminophenol—0.12 g
m-diaminoanisole sulfate—0.07 g
Resorcine—0.4 g
m-aminophenol—0.15 g
p-toluylene diamine—1.3 g
Trilon B—0.23 g
Sodium bisulfite (d=1.32)—1 g
Hydroquinone—0.1 g
1-phenyl 3-methyl 5-pyrazolone—0.16 g
Water, qsp—100 g By using similar procedures as in previous examples, there is obtained a dark blonde shade.

Polymer R consists of units of formula I wherein $A=(CH_2)_3$, $B=(CH_2)_4$, $R_1=R_2=C_3H_7$, $R_3=R_4=CH_3$ and $X=Br$.

EXAMPLE 27

The following liquid dye composition was prepared:
Eutanol G—11.5 g
Oleic diethanolamide—8.5 g
Mergital OC. 30—2 g
Oleic acid—20 g
Benzyl alcohol—10.5 g
Ethyl alcohol (96%)—11 g
Polymer F—1.5 g
Ammonia, 22° Be—17.5 ml
p-toluylene diamine—0.78 g
p-aminophenol—0.17 g
2-methyl 5-methoxy paraphenylene diamine—0.03 g m-diaminoanisole sulfate—0.07 g
Resorcine—0.4 g
m-aminophenol—0.08 g
6-hydroxy benzomorpholine—0.022 g
Hydroquinone—0.16 g
Trilon B—0.3 g
Sodium bisulfite (d=1.32)—1 g
Water, qsp—100 g By using similar procedures as in previous examples, there is obtained a light chestnut shade.

EXAMPLE 28

The following liquid dye composition was prepared:
Triethanolamine laurylsulfate (40% active material)—2 g
Eutanol G—16 g
Oleic diethanolamide—6 g
Mergital OC. 30—3 g
Oleic acid—15 g
Monoethanolamine—3 g
Benzyl alcohol—6 g
Ethyl alcohol—10 g
Polymer S—2.4 g
Ammonia, 22° Be—10 ml
p-aminophenol—0.28 g
Resorcine—0.7 g
m-aminophenol—0.6 g
Trilon B—0.2 g
Hydroquinone—0.05 g
p-toluylenediamine—0.15 g
sodium bisulfite (d=1.32)—1.2 g
1-phenyl 3-methyl 5-pyrazolone—0.15 g
Water, qsp—100 g By using similar procedures as in previous examples, there is obtained a light chestnut shade.

Polymer S consists of units of formula I wherein $A=(CH_2)_6$; $B=(CH_2)_3$; $R_1=R_2=CH_3$, $R_3=R_4=CH_2CH_2OH$ and $X=Br$.

What is claimed is:
1. A hair dyeing composition which comprises an oxidation dye in an amount effective to dye said hair and a vehicle, said vehicle comprising
   a fatty acid present in an amount of 5 to 30 percent by weight of said composition, said fatty acid having 12 to 20 carbon atoms;
   an alkalizing agent in excess of the stoichiometric amount of said agent which is effective to neutralize the fatty acid, said excess being from 1 to 30 percent of the total weight of said composition;
   benzyl alcohol present in an amount from 2 to 20% by weight of the composition so that an admixture of said composition with hydrogen peroxide has a creamy consistency; and
   1 to 15% by weight of the composition of a cationic polymer having repeating units of the formula

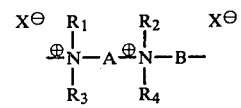

wherein
each of $R_1$, $R_2$, $R_3$ and $R_4$ is identical and is alkyl of 1 to 3 carbon atoms; or wherein $R_1$ is identical to $R_2$, $R_3$ is identical to $R_4$, and $R_2$ is different from $R_3$, then each of $R_1$ and $R_2$ is alkyl of 1 to 3 carbon atoms and each of $R_3$ and $R_4$ is hydroxyalkyl containing 1 to 3 carbon atoms;

each of A and B is linear or branched alkylene or linear or branched alkenylene of 2 to 20 carbon atoms; —$(CH_2)_n$—O—$(CH_2)_n$—; —$(CH_2)_m$—NH—CO—NH—$(CH_2)_m$—; —$CH_2CHOH$—$CH_2$— or —$CH_2C_6H_4$—$CH_2$—; n and m are whole numbers, each of n and m being equal to 2 or 3; and X is an anion.

2. A composition for use in dyeing hair comprises at least one oxidation dye present in an amount of 0.001 to 10 percent by weight thereof and a vehicle, said vehicle comprising at least one fatty acid present in an amount of 5 to 30 percent by weight of said composition;

at least one alkalizing agent in excess of the stoichiometric amount of said agent which is effective to neutralize the fatty acid, said excess being from 1 to 30 percent of the total weight of said composition;

benzyl alcohol present in an amount of from 2 to 20 percent by weight of the composition so that an admixture of said composition with hydrogen peroxide has a creamy consistency; and 1 to 15 percent by weight of the composition of a cationic polymer having repeating units of the formula

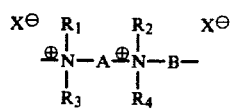

and selected from the group consisting of (1) a polymer wherein A is $(CH_2)_3$, B is $(CH_2)_6$, each of $R_1$, $R_2$, $R_3$ and $R_4$ is $CH_3$ and X is Br,
(2) a polymer wherein A is $(CH_2)_3$, B is $(CH_2)_6$, each of $R_1$, $R_2$, $R_3$ and $R_4$ is $CH_3$ and X is Cl,
(3) a polymer wherein A is $(CH_2)_6$, B is $(CH_2)_3$, each of $R_1$, $R_2$, $R_3$ and $R_4$ is $CH_3$ and X is Br,
(4) a polymer wherein A is $(CH_2)_6$, B is $(CH_2)_4$, each of $R_1$, $R_2$, $R_3$ and $R_4$ is $CH_3$ and X is Br,
(5) a polymer wherein A is $(CH_2)_2$, B is $(CH_2)_4$, each of $R_1$, $R_2$, $R_3$ and $R_4$ is $CH_3$ and X is Br,
(6) a polymer wherein A is $(CH_2)_6$, B is $(CH_2)_5$, each of $R_1$, $R_2$, $R_3$ and $R_4$ is $CH_3$ and X is Br,
(7) a polymer wherein A is $(CH_2)_3$, B is $(CH_2)_4$, each of $R_1$, $R_2$, $R_3$ and $R_4$ is $CH_3$ and X is Br,
(8) a polymer wherein A is $(CH_2)_3$, B is $(CH_2)_5$, each of $R_1$, $R_2$, $R_3$ and $R_4$ is $CH_3$ and X is Br,
(9) a polymer wherein A is $(CH_2)_2$, B is $(CH_2)_5$, each of $R_1$, $R_2$, $R_3$ and $R_4$ is $CH_3$ and X is Br,
(10) a polymer wherein A is $(CH_2)_3$—O—$(CH_2)_3$, B is $CH_2CHOH$—$CH_2$, each of $R_1$, $R_2$, $R_3$ and $R_4$ is $CH_3$ and X is Br,
(11) a polymer wherein A is

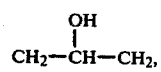

B is $(CH_2)_4$, each of $R_1$, $R_2$, $R_3$ and $R_4$ is $CH_3$ and X is Br,
(12) a polymer wherein A is $(CH_2)_6$, B is $(CH_2)_2$—O—$(CH_2)_2$, each of $R_1$, $R_2$, $R_3$ and $R_4$ is $CH_3$ and X is Br,
(13) a polymer wherein A is —$(CH_2)_3$—NHCONH$(CH_2)_3$, B is —$CH_2$—$CH_2$—O—$CH_2$—$CH_2$—, each of $R_1$, $R_2$, $R_3$ and $R_4$ is $CH_3$ and X is Cl,
(14) a polymer wherein A is —$(CH_2)_3$—NH—CONH—$(CH_2)_3$—, B is —$CH_2CHOHCH_2$—, each of $R_1$, $R_2$, $R_3$ and $R_4$ is $CH_3$ and X is Cl,
(15) a polymer wherein A is —$(CH_2)_3$—NH—CONH—$(CH_2)_3$—, B is

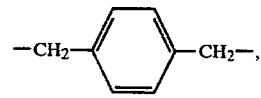

each of $R_1$, $R_2$, $R_3$ and $R_4$ is $CH_3$ and X is Br,
(16) a polymer wherein A is —$(CH_2)_3$—NH—CONH—$(CH_2)_3$, B is —$CH_2$—CH=CH—$CH_2$—, each of $R_1$, $R_2$, $R_3$ and $R_4$ is $CH_3$ and X is Br,
(17) a polymer wherein A is —$(CH_2)_3$—NH—CONH—$(CH_2)_3$, B is $(CH_2)_6$, each of $R_1$, $R_2$, $R_3$ and $R_4$ is $CH_3$ and X is Cl,
(18) a polymer wherein A is $(CH_2)_3$, B is $(CH_2)_4$, each of $R_1$, $R_2$ and $R_3$ is $CH_3$, $R_4$ is $C_4H_9$ and X is Br,
(19) a polymer wherein A is $(CH_2)_3$, B is $(CH_2)_4$, each of $R_1$, $R_2$ and $R_4$ is $CH_3$, $R_3$ is $C_3H_7$ and X is Br,
(20) a polymer wherein A is $(CH_2)_3$, B is $(CH_2)_4$, each of $R_1$ and $R_3$ is $CH_3$, each of $R_2$ and $R_4$ is $C_4H_9$ and X is Br,
(21) a polymer wherein A is $(CH_2)_3$, B is $(CH_2)_6$, each of $R_1$ and $R_3$ is $C_2H_5$, each of $R_2$ and $R_4$ is $CH_3$ and X is Br,
(22) a polymer wherein A is $(CH_2)_3$, B is $(CH_2)_4$, each of $R_1$ and $R_2$ is $C_3H_7$, each of $R_3$ and $R_4$ is $CH_3$ and X is Br, and
(23) a polymer wherein A is $(CH_2)_6$, B is $(CH_2)_3$, each of $R_1$ and $R_2$ is $CH_3$, each of $R_3$ and $R_4$ is $CH_2CH_2OH$ and X is Br.

3. A composition of claim 1, wherein each of $R_1$, $R_2$, $R_3$ and $R_4$ is methyl, ethyl or propyl or each of $R_3$ and $R_4$ is 2-hydroxyethyl, 2-hydroxypropyl or 3-hydroxypropyl; A and B are identical or different and each of A and B is of the formula $$-(CH_2)_y-CH(E)-(CH_2)_x-CH(K)-(CH_2)_t-$$

in which x, y and t are whole numbers which range from 0 to 11, wherein the sum of (x+y+t) is at least 0 and less than 18, and each of E and K is hydrogen or aliphatic of less than 18 carbon atoms and X is Br or Cl.

4. A composition of claim 1, wherein A, B or both A and B are alkylene of the formula $$-(CH_2)_{n1}-CH=CH-(CH_2)_{n2}-$$

wherein each of $n_1$ and $n_2$ is a whole number ranging from 0 to 18 and wherein the sum of $n_1$ and $n_2$ is less than or equal to 18.

5. The composition of claim 1 wherein said fatty acid is lauric acid, palmitic acid, myristic acid, stearic acid, isostearic acid, oleic acid, arachic acid, ricinoleic acid, phenylstearic acid, linoleic acid or mixtures thereof.

6. The composition of claim 1, wherein said alkalizing agent is sodium hydroxide, potassium hydroxide, ammonia, monoethanolamine, diethanolamine, triethanolamine or mixtures thereof.

7. The composition of claim 1, which contains 1.5 to 10% by weight of said cationic polymer.

8. The composition of claim 1, which contains 5 to 15% by weight of benzyl alcohol.

9. The composition of claim 1, which contains 0.001 to 10% by weight of an oxidation dye.

10. The composition of claim 1, which is in the form of a liquid and contains a liquid fatty acid or liquid mixture of fatty acids.

11. The composition of claim 1, which has a pH of from 5 to 11.

12. The composition of claim 10 wherein the fatty acid is oleic acid, isostearic acid or mixtures thereof.

13. The composition of claim 10 or 12, wherein the alkalizing agent is a mixture of ammonia and monoethanolamine or di-ethanolamine, the monoethanolamine or diethanolamine being present in a stoichiometric amount with respect to said fatty acid and the ammonia being present in an amount ranging from 7 to 15% by weight of the composition.

14. The composition of claim 10, wherein said benzyl alcohol is present in an amount from 5 to 15% by weight of said composition, said benzyl alcohol being in a solvent at a concentration of 2 to 20%.

15. The composition of claim 14, which includes a solvent which is a lower aliphatic alcohol or a glycol.

16. The composition of claim 1, admixed with an excess of a solution of an oxidizing agent.

17. The composition of claim 15, wherein said solvent is ethyl alcohol, propyl alcohol, isopropyl alcohol, propylene glycol, methyl glycol, hexylene glycol or monoethylester of diethylene glycol.

18. The composition of claim 9, wherein said oxidation dye ranges from 0.03 to 5% by weight of said composition.

19. The composition of claim 14, wherein said concentration is from 5 to 15%.

20. The composition of claim 11, wherein said pH is from 8 to 10.5.

21. A process of dyeing hair, comprising applying the composition of claim 16 to hair, said composition being in an amount sufficient to dye said hair.

* * * * *